(12) United States Patent
Burm et al.

(10) Patent No.: US 6,624,147 B1
(45) Date of Patent: Sep. 23, 2003

(54) INHIBITORS OF PRENYLATED PYROPHOSPHATE CONSUMING ENZYMES

(75) Inventors: Brigitte Elisa Anna Burm, Zeist (NL); Nicolette Voskuyl, Leiden (NL); Hans Van Den Elst, Hillegom (NL); Elsbet Jantine Pieterman, Leiden (NL); Louis Hartog Cohen, Breukelen (NL); Mark Overhand, Leiden (NL); Gijsbert Arie Van Der Marel, Leiden (NL); Jacobus Hubertus Van Boom, Oegstgeest (NL)

(73) Assignees: Rijksuniversiteit Leiden, Leiden (NL); Nederlandse Organisatie voor Toegepast-Natuurwetenschappelijk Onderzoek Tno, Delft (NL)

( * ) Notice: Subject to any disclaimer, the term of this patent is extended or adjusted under 35 U.S.C. 154(b) by 0 days.

(21) Appl. No.: 09/671,298

(22) Filed: Sep. 28, 2000

(30) Foreign Application Priority Data

Sep. 28, 1999 (EP) .............................. 99203170

(51) Int. Cl.$^7$ .................................. C07K 5/06
(52) U.S. Cl. .......................... 514/19; 530/331; 514/18; 562/571
(58) Field of Search ............................ 562/571; 514/18, 514/19; 530/331

(56) References Cited

U.S. PATENT DOCUMENTS 4,806,473 A * 2/1989 Johansen ..................... 435/71
RE33,635 E * 7/1991 Matsumoto ................... 435/18

FOREIGN PATENT DOCUMENTS

| EP | 0540782 A1 | 5/1993 |
| WO | WO 9509001 | 4/1995 |
| WO | WO 9600736 | 1/1996 |
| WO | WO 9610011 | 4/1996 |

OTHER PUBLICATIONS

Cohen, Biochemical Pharmacology 57, 365, 1999.*
Herman S. Overkleeft et al., "Design and Synthesis of a Protein: Farnesyltransferase Inhibitor based on Sugar Amino Acids," Tetrahedron Letters 40 (1999), pp. 4103–4106.
Daniele M. Leonard, "Ras Farnesyltransferase: A New Therapeutic Target," Journal of Medicinal Chemistry, vol. 40, No. 19, Sep. 12, 1997, pp. 2971–2990.
D.M. Leonard et al., "Histidine–(N–benzylglycinamides): Structure–activity studies optimizing potency against ras farnesyl transferase," Proceedings of the Annual Meeting of the American Association for Cancer Research, vol. 38, Apr. 12, 1997, p. 350 (Abstract Only).

* cited by examiner

*Primary Examiner*—Christopher S. F. Low
*Assistant Examiner*—David Lukton
(74) *Attorney, Agent, or Firm*—Young & Thompson

(57) ABSTRACT

Novel peptide-like FPP-analogues suitable for inhibiting protein:prenyl transferases, such as protein:geranylgeranyl transferase-1, and other prenyl pyrophosphate-consuming enzymes such as squalene synthase and geranylgeranyl pyrophosphate synthase are disclosed.

20 Claims, 1 Drawing Sheet

Scheme 1
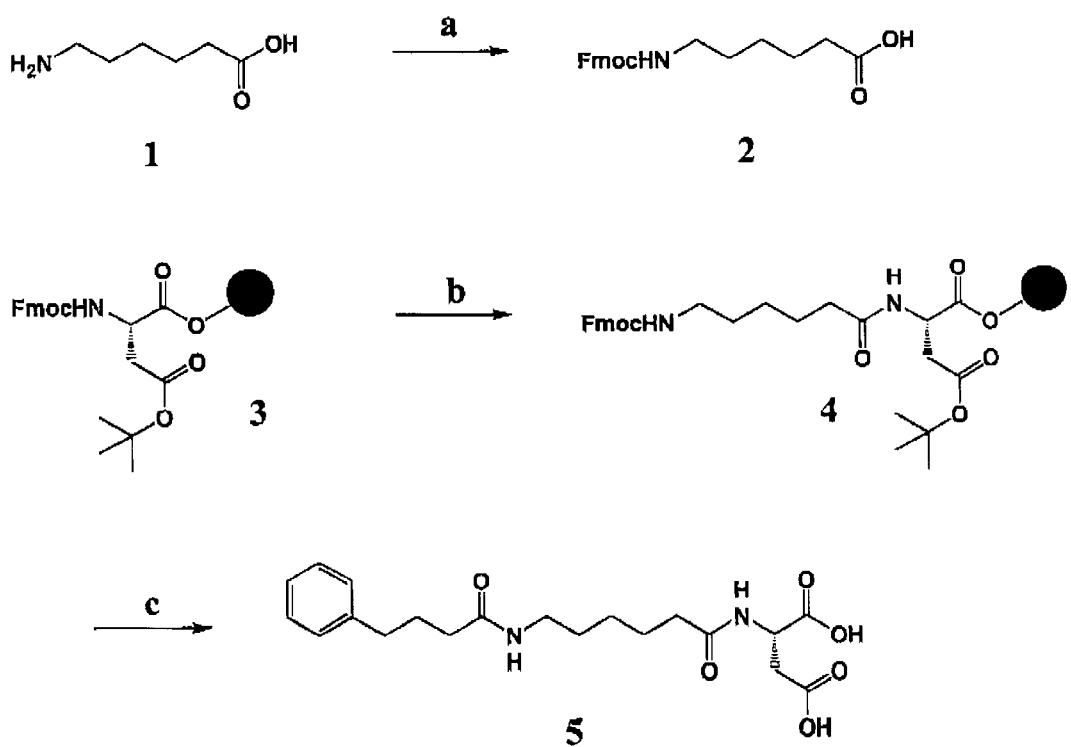
a) FmocCl, NaHCO$_3$ (85 %); b) *i*. 20 % piperidine in DMF
*ii*. compound 2 (5 equiv.), BOP, HOBt, DiPEA, NMP;
c) *i*. 20 % piperidine in DMF *ii*. 4-phenylbutyric acid (5 equiv.),
BOP, HOBt, DiPEA, NMP *iii*. TFA/triisopropylsilane 99.5/0.5.

INHIBITORS OF PRENYLATED PYROPHOSPHATE CONSUMING ENZYMES

The present invention relates to peptide analogues which inhibit prenylated pyrophosphate-consuming enzymes. Prenylated pyrophosphate consuming enzymes are understood to comprise protein:farnesyl transferases, protein:geranylgeranyl transferases and several other enzymes involved in the biosynthesis of terpenes, such as farnesyl pyrophosphate synthase, squalene synthase and geranylgeranyl pyrophosphate synthase.

Prenylated pyrophosphates, i.e. all-trans-farnesyl pyrophosphate (FPP) and all-trans-geranylgeranyl pyrophosphate (GGPP), are substrates for a number of different enzymes. Protein:farnesyl transferase (PFT) is an enzyme which uses FPP to catalyse the farnesylation of cysteine residues near the C-terminus of certain proteins. The enzyme geranylgeranyl pyrophosphate synthase (GGPPS) uses FPP as a substrate in the production of geranylgeranyl pyrophosphate (GGPP), which is subsequently used in the synthesis of geranylgeranylated proteins mediated by the enzymes protein:geranylgeranyl transferase 1 and 2 (PGGT-1 and 2).

Several of these prenylated (i.e. farnesylated and/or geranylgeranylated) proteins were identified as belonging to groups of related proteins: e.g. the nuclear lamins, low molecular weight GTP binding proteins (G-proteins), such as the ras-oncogene proteins and the γ-subunit of heterotrimeric G-proteins (Schafer et al., *Science* 245 (1989) 379–385). Lamins and $p21^{ras}$ proteins, 188 or 189 amino acid proteins which possess the consensus CaaX motif (C=cysteine, a=any amino acid having an aliphatic side chain and X=methionine, serine, glutamine or alanine) at the C-terminus, are farnesylated. Other small G-proteins, that have the consensus CaaL motif (L=leucine) such as Rho and several members of the rab proteins having C-terminal CC/CXC motifs, and also heterotrimeric G-protein γ-subunits are geranylgeranylated.

G-proteins are involved in the receptor-mediated transduction of signals (such as growth modulation signals) over the plasma membrane, and other prenylated proteins, not yet identified, may have a function in cell cycle progression. The prenylation of these proteins seems to play a role in their association with membranes and nuclear envelopes, where they are processed further and/or perform their function. This was shown for example by blocking the mevalonate synthesis by HMG-CoA reductase inhibitors, which prevented proteolytic processing of the lamin A precursor (Beck et al., *J. Cell. Biol.* 110 (1990) 1489–1499) or resulted, in other studies, in the accumulation of non-prenylated $p21^{ras}$ precursor and the loss of transforming activity of oncogenic ras proteins. A review of the post-translational modification of proteins by isoprenoids in mammalian cells is given by Maltese W. A. in *FASEB J.* 4 3319–3329 (1990). The latter observation triggered the search for specific inhibitors of the farnesylation of $p21^{ras}$ in order to prevent its action in cells, where over-expression of this protein leads to tumour development, such as in colon carcinomas.

We have shown that FPP-analogues, which are in vitro inhibitors of PFT and/or PGGT-1 are able to inhibit the proliferation of human arterial smooth muscle cells in culture (Cohen et al. *Biochem. Pharm.* 57 (1999), 365–373) and are therefore potential inhibitors of the process of restenosis after percutaneous transluminal coronary angioplasty. The proliferation of smooth muscle cells plays a major role in the latter process.

Very recently it was shown that inhibition of the cellular GGPP synthesis in specific bone cells (osteoclasts) is the possible mechanism of action of anti-osteoporosis drugs (Van Beek, E. *Biochem. Biophys. Res. Commun.* 255, (1999), 491–494 and Van Beek, E. *J. Bone and Min. Res.* 14 (1999), 722–729). So, inhibitors of GGPPS and/or PGGT-1 and/or -2 may be active as anti-osteoporosis drugs as well.

Furthermore, G-proteins of the rab-family are involved in the regulation of intracellular protein traffic and secretion. In addition, prenylated proteins seem to play a role in the translational control of HMG-CoA reductase, the rate limiting enzyme of the isoprene and subsequent cholesterol biosynthesis. Squalene synthase (SS), the first pathway-specific enzyme in the biosynthesis of cholesterol, catalyses the reductive dimerisation of two molecules of FPP to produce squalene. Much attention has been directed to the development of inhibitors of SS with the aim to lower elevated blood plasma levels of cholesterol, one of the risk factors for cardiovascular diseases.

EP-A-540782 describes inhibitors for protein:farnesyl transferase based on prenyl pyrophosphate analogues. A review of new therapeutic methods based on protein:farnesyl transferase and inhibitors thereof are described by Leonard in *J. Med. Chem.* 40 (1997), 2971–2990. Furthermore, we recently (Overkleeft et al. *Tetrahedron Let.* 40 (1999) 4103–4107) described inhibitors of protein:prenyl transferases based on binding in the CaaX pocket of the enzyme concerned (see also EP-A-1028117).

Novel analogues of prenyl pyrophosphate have been found according to the invention, which are inhibitors of prenylated pyrophosphate consuming enzymes (e.g. PFT, PGGT-1 and 2, GGPPS and SS) presumably by binding in the FPP pocket. The analogues are defined in the appending claims with reference to formulae 1 (A—B—D) and 2 (A—B—B'—D). The novel prenylated pyrophosphate-based inhibitors contain unnatural amino acid moieties which have the potential to be unsusceptible towards enzymatic degradation. These novel inhibitors are composed of amino acid derivatives which are ideally suited for the construction of a compound library via a combinatorial approach. Furthermore their peptide-like structure allows for easy access to bisubstrate analogues, in which the new FPP analogues are connected to CaaX box analogues, as defined in the appending claims.

BRIEF DESCRIPTION OF DRAWINGS

FIG. 1 depicts the synthesis of protein:farnesyl and/or geranylgeranyl transferase inhibitors.

DETAILED DESCRIPTION OF THE INVENTION

Important features of the peptide-like FPP-analogues of the invention are the presence of a hydrophobic region (part A), a spacer moiety comprising one or two (un)natural amino acids (parts B and B') and, most preferably, a negatively charged amino acid residue at the C-terminus (part D). The hydrophobic region contains at least six carbon atoms (including further groups such as a carbonyl or oxymethylene group) up to about 24 carbon atoms, preferably between 8 and 18 carbon atoms, and may comprise alkyl, alkenyl, cycloalkyl, cycloalkenyl or aryl groups which may also contain heteroatoms. These groups may contain substituents, which are preferably non-polar, such as $C_1$–$C_4$ alkyl, $C_1$–$C_4$ alkoxy, and the like. Examples of non-aromatic moieties are hexyl, isooctyl, decyl, dodecyl, cyclopentenyl, cyclohexyl, methylcyclohexyl, tetrahydropyranyl, and extensions thereof such as cyclohexylmethylcarbonyl, cyclohexylethyl, lauroyl, and the like. Aryl and especially aralkyl groups are preferred. Aromatic moieties include phenyl, tolyl, methoxyphenyl, isopropoxyphenyl, methylenedioxyphenyl, tetrahydronaphthyl, pyridyl, pyrimidyl, furyl, imidazolyl, thiazolyl, naphthyl, phenoxyphenyl, indolyl, anthryl, and the corresponding benzoyl, phenylethyl, cinnamyl and longer aralk(en)yl derivatives. Examples of part A further include phenyl-($C_1$–$C_6$)-alkanoyl, benzoylaminoacetyl, furoyl-aminoacetyl, β-(benzoylamino)acryloyl, N-(benzyloxycarbonyl)-histidinoyl, and naphthyl-acetyl.

The total length of the spacer (parts B and B') is preferably 6–12 atoms for PFT inhibitors and longer, up to 18 atoms, for PGGT-1 or -2 inhibitors, the spacer may optionally contain multiple amide/amine linkages as well as other heteroatoms (e.g. S, O, etc.) and may be flexible or conformationally restricted. Preferably, B and/or B are residues of unnatural amino acids, such as β-, γ-, δ-, etc. aliphatic amino acids or amino acids containing a cyclohexylene or phenylene moiety between the amino group and the carboxyl group. The residue at the carboxy terminus (D) of the invented peptide analogues must contain one or more functionalities that can be deprotonated (i.e. negatively charged) under physiological conditions. The negatively charged groups are preferably carboxylic acids, phosphates, phosphonates, sulfonates and/or sulfates, most preferably carboxylates or phosphates. The terminal carboxy group of part D may be a carboxy group as such (or a metal salt thereof) or it may esterified (e.g. with an alcohol or a hdyroxyacid such as methanol, ethanol, glycolic or malic acid) or amidated or with peptide-like groups such as a single amino acid, possibly carrying a further negatively charged group (e.g. glycine, aspartic acid, glutamic acid, phosphoserine) or any oligopeptide, preferably a tetrapeptide containing a sugar amino acid derivative as described in EP-A-1028117.

Preferred peptide analogues according to the invention are analogues that are expected to be specific for the inhibition of farnesylation or geranylgeranylation processes as a function of their total length. It is anticipated that specific SS and GGPPS inhibitors will be obtained from the screening of a compound library due to the different mechanisms in which these enzymes convert FPP.

The peptide analogues according to the invention can be prepared in a manner which is known per se. For example, they may be prepared by starting with the suitably protected building block having the formula:

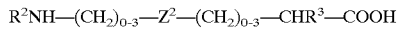

and coupling this unit to the terminal units:

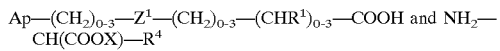

Compounds in which Y is $CH_2$, rather than carbonyl, can be obtained by reduction or reductive amination, in a manner known per se. For example, these analogues may be prepared by starting with the suitably protected central unit having the formula:

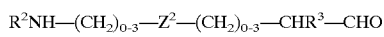

And reacting this unit under reductive conditions with the terminal units:

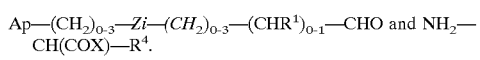

It was found that the peptide analogues according to the invention are capable of inhibiting the protein-farnesylation and/or geranylgeranylation process. Because of their ease of synthesis various inhibitors can be easily generated through combinatorial chemistry. The bioavailability, stability against enzymatic degradation and inhibitory activity of these novel inhibitors will be better than for previously reported compounds.

The peptide-like FPP-analogues described above are useful as an active substance in a pharmaceutical composition intended to interfere with protein prenylation or cholesterol biosynthesis. As such, they are useful as inhibitors in processes such as oncogenesis and other unwanted cell proliferation, e.g. in restenosis or atherosclerosis, and furthermore as suppressants of aberrant high signal transduction. Also, they can be used as anti-osteoporosis drugs and drugs to lower elevated plasma levels of cholesterol.

The pharmaceutical compositions containing the analogues according to the invention may be formulated in a usual way, e.g. by associating the inhibitors with a suitable solid or liquid carrier and optional adjuvants or other active components. The composition may be suitable for oral administration (capsule, pill, tablet, gel, powder, sachet, syrup, solution, dispersion etc.) or may be an injectable solution or another administration form. The composition may be administered to mammalians including man, in a dose which depends on the particular purpose of the administration and other conditions well known to the skilled person. A suitable dose is e.g. from 1 to 500 mg/kg body weight, especially from 10 to 200 mg/kg body weight. A dose can be administered in a single dosage or in several daily dosages.

The analogues of the invention can also be used in diagnostics procedures involving of assaying protein:prenyltransferase activity in a biological sample or any other prenyl pyrophosphate consuming enzyme, by contacting the sample in which such activity is be determined with the peptide analogue and further reagents, enzyme substrates, labels (dyes, radioactive or fluorescent labels, antibodies etc.), diluents and the like as necessary for detecting the interaction of the peptide analogue with the enzyme under investigation.

EXAMPLE 1

Synthesis of Protein:farnesyl and/or Geranylgeranyl Transferase Inhibitors

Fmoc-Asp(O-t-Bu)-wang resin 3 (0.6 mmol/g, Novabiochem) was treated with 20% piperidine in dimethylformamide (DMF) and subsequently coupled with compound 2 (5 equiv.) under a standard solid phase peptide synthesis protocol (Atherthon et al. *Solid Phase Synthesis: A Practical Approach*, IRL Press: Oxford, 1989) i.e. benzotriazole-1-yl-oxy-tris-(dimethylamino)phosphonium hexafluorophosphate (BOP), 1-hydroxybenzotriazole (HOBt), diisopropylethylamine (DIPEA) in N-methylpyrrolidone (NMP). The obtained compound 4 was subsequently treated with 20% piperidine in DMF, coupled with 4-phenylbutyric acid (Aldrich) using the same reagents as mentioned above and cleaved from the solid support with trifluoroacetic acid (TFA)/triisopropylsilane 99.5/0.5 v/v %. The obtained compound 5 was purified using preparative HPLC (Lichrosphere 100 RP18 end-capped (5μ), 10×250 mm, elution: linear gradient of 80% acetonitrile/water/0.1% TFA) and fully characterised with spectroscopic techniques.

EXAMPLE 2

Assays of Protein:farnesyl Transferase and Protein:geranylgeranyl Transferase 1

PFT activity was determined using a C-terminal peptide of pre-p21$^{N-ras}$ coupled to sepharose beads as substrate (pepAsep) as described previously (Cohen et al. *Biochem. Pharmacol.* 57 (1999), 365–373). The experimental conditions (25 reaction mixture) were as follows: 80 pmol/25 μL epharose-coupled peptide, 0.7 μM of [$^3$H]-FPP (American Radiolabeled Chemicals Inc.; specific radioactivity 15 Ci/mmol) and 13 μL of rat brain enzyme preparation. Incubation was performed at 37° C. for 30 min. For the determination of IC$_{50}$ values of the FPP analogues, the assay was performed three times in the presence of different concentrations of compound 5 (example 1) in duplicate.

Determination of PGGT-1 activity was performed in a similar manner as described for PFT activity and has also been described previously (Cohen et al. *Biochem. Pharmacol.* 57 (1999), 365–373). The same C-terminal peptide was used, except that the C-terminal methionine was replaced by leucine (pepCsep). The experimental conditions were as follows: 25 μL incubation mixture contained 2.5 μL (1 nmol) pepCsep, 1 μM [$^3$H]-GGPP (American Radiolabeled Chemicals Inc.; specific radioactivity 15 Ci/mmol), 3 μL of bovine brain enzyme preparation, 50 μM ZnCl$_2$, 0.5 mM MgCl$_2$, 1 mM dithiothreitol, 0.004% Triton X-100, 50 mM Tris-HCl (pH 7.4). Incubation was performed at 37° C. for 40 min. with continuous shaking. For the determination of IC$_{50}$ values of the GGPP analogues, the assay was performed three times in the presence of at least five different concentrations of the compound 5 in duplicate.

EXAMPLE 3

According to the procedure as outlined in example 1, the following representative compounds have been prepared, with PFT IC$_{50}$ values being indicated. The compound with internal reference number TR 060 corresponds to compound 5 of examples 1 and 2.

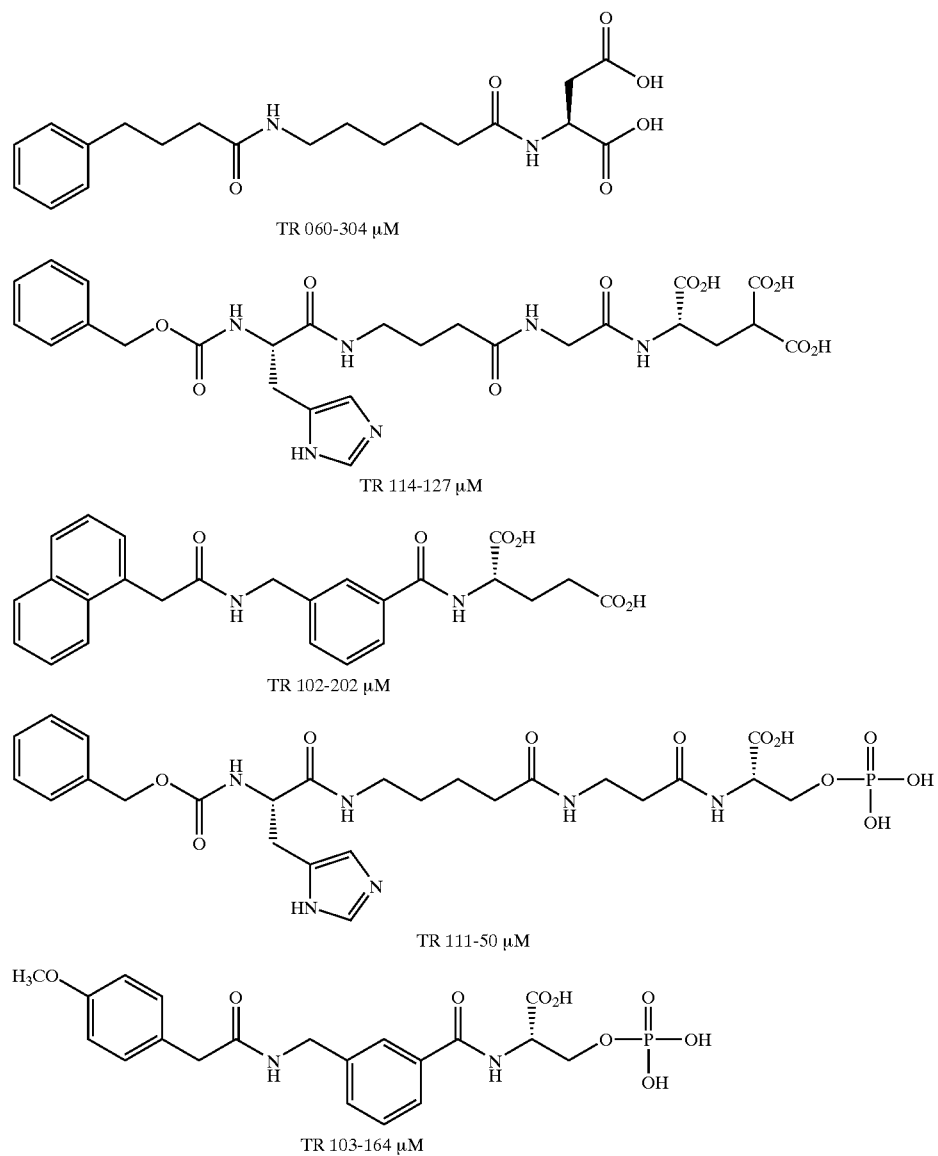

-continued

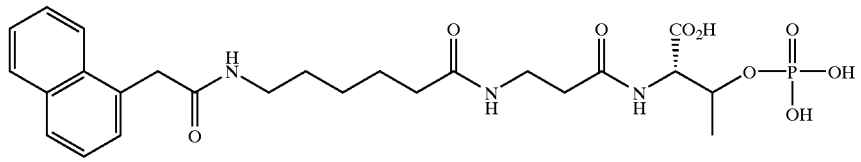
TR 112-354 μM

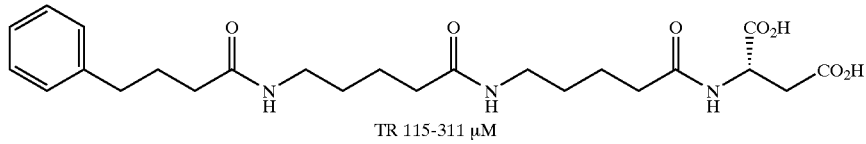
TR 115-311 μM

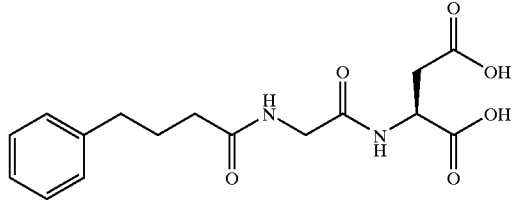
TR 058-797 μM

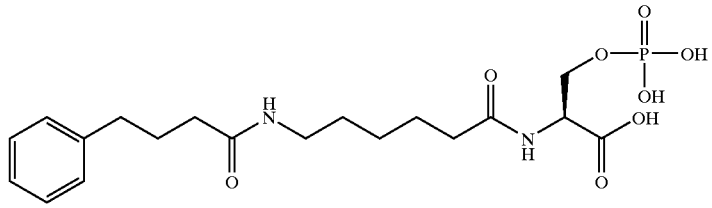
TR 074-76 μM

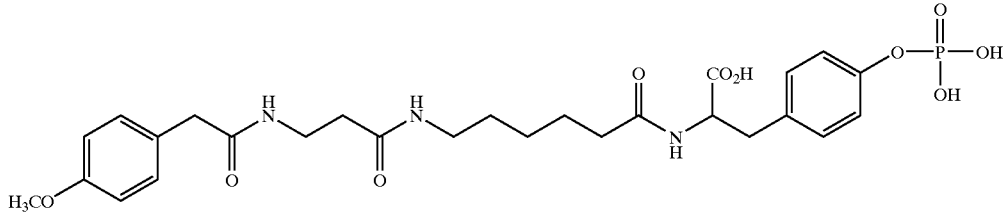
TR 113-286 μM

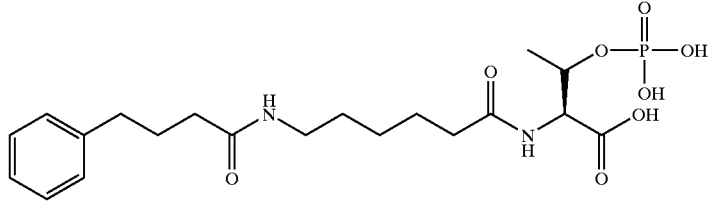
TR 076-672 μM

What is claimed is:

1. An inhibitor of a prenylpyrophosphate-consuming enzyme of formula I or II:

A—B—D    I

A—B—B'—D    II wherein:

A is Ap—(CH$_2$)$_{0-3}$—Z$^1$—(CH$_2$)$_{0-3}$—(CHR$^1$)$_{0-1}$—Y—

B and B' are independently —NR$^2$—(CH$_2$)$_{0-3}$—Z$^2$—(CH$_2$)$_{0-3}$—CHR$^3$—Y—, or

with the proviso that in formula II, at least one of B and B' contains at least 4 chain atoms and in formula I, B contains at least 4 chain atoms;

D is —NH—CH(COX)—R$^4$ in which:

Ap is a hydrocarbon group containing at least 5 carbon atoms, optionally substituted with C$_{1-4}$ alkyl, C$_{1-4}$ alkoxy, halogen, methylenedioxy, aryl or aryloxy;

$R^1$ is hydrogen, or $C_{1-4}$ alkyl optionally substituted with aryl or heteroaryl;

$R^2$ is hydrogen, or $C_{1-4}$ alkyl optionally substituted with aryl or heteroaryl;

$R^3$ is hydrogen, or $C_{1-4}$ alkyl optionally substituted with aryl, heteroaryl or amino;

$R^4$ is $C_{1-4}$ alkyl, which is substituted with at least one group selected from carboxyl, phosphonic acid ($PO_3H_2$), phosphoric acid ($OPO_3H_2$), sulfonic acid ($SO_3H$), sulfuric acid ($OSO_3H$), carboxyphenyl, sulphophenyl ($C_6H_4SO_3H$), phosphonophenyl ($C_6H_4PO_3H_2$) or phosphoxyphenyl ($C_6H_4OPO_3H_2$) groups;

X is selected from the group consisting of OH, OM, O—$C_{1-4}$ alkyl, NH-peptidyl, NH—$CHR^5$—CT—NH—W—CT—NH—CH($COOR^6$)—C($R^7R^8$)$R^9$ and O—$C_{1-4}$ alkyl in which the O—$C_{1-4}$ group is substituted with hydroxyl or carboxyl, wherein:

M is an alkali metal;

$R^5$ is hydrogen, $C_{1-3}$ alkyl, mercaptomethyl or a protected mercaptomethyl group;

$R^6$ is hydrogen or $C_{1-4}$ alkyl;

$R^7$ is hydrogen or $C_{1-4}$ alkyl $R^8$ is hydrogen or $C_{1-4}$ alkyl $R^9$ is hydrogen or $C_{1-6}$ alkyl optionally substituted with hydroxyl, phenyl, hydroxyphenyl, indolyl, imidazolyl, mercapto, methylthio, amion, carboxyl, carbamoyl, ureido, amidino or guanidine;

T is oxo or two hydrogens; and

W is a sugar amino acid analogue of the following formula:

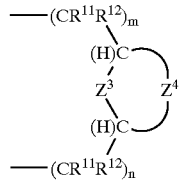

in which:

$R^{11}$ and $R^{12}$ are independently hydrogen or $C_{1-4}$ alkyl;

$Z^3$ is oxygen, sulphur, imino or $C_{1-6}$ alkyl-, aryl- or acylimino;

$Z^4$ is a direct bond or a saturated or unsaturated $C_{1-4}$ alkylene chain, optionally interrupted by one or more oxygen, sulphur or nitrogen atoms and optionally substituted with hydroxy, oxo, $C_{1-4}$ alkyl, $C_{1-4}$ alkylidene, $C_{1-4}$ alkoxy, allyloxy, benzyloxy, $C_{1-6}$ acyloxy, $C_{1-3}$ alkyl(id)enedioxy, amino, $C_{1-4}$ alkylamino or $C_{1-4}$ hydroxyalkyl;

(H) represents a hydrogen if $Z^4$ is saturated at the corresponding C atom and is absent if $Z^4$ is unsaturated at the corresponding C atom;

m is 0, 1 or 2;

n is 0 or 1;

each Y is independently carbonyl or methylene;

$Z^1$ is —$CH_2$—$CHR^{10}$—, —CH═$CR^{10}$—($R^{10}$ is H or $C_{1-4}$ alkyl), —C≡C—, 1,2-, 1,3- or 1,4-cyclohexylene or -phenylene, —CO—, —CO—NH—, —O—CO—NH, or —O— or a direct bond;

$Z^2$ is —$CH_2$—$CHR^{10}$—, —CH═$CR^{10}$—, —C≡C—, 1,2-, 1,3- or 1,4-cyclohexylene or 1,2-, 1,3- or 1,4 phenylene, —O—, —S—, —NH—, or a direct bond;

or a salt or ester thereof.

2. The inhibitor according to claim 1, complying with formula 1, in which one or more of the following definitions apply:

A is Ap—$(CH_2)_{0-3}$—Z'—$(CH_2)_{0-3}$—$(CHR')_{0-1}$—Y;

Ap is an optionally substituted aryl group;

$R^1$ is hydrogen, methyl or imidazolylmethyl;

at least one of $R^2$ and $R^3$ is hydrogen;

at least one of $Z^1$ and $Z^2$ is a direct bond;

$R^4$ is methyl, ethyl or benzyl substituted with one or two COOH or $OPO_3H_2$;

X is OH;

Y is carbonyl.

3. The inhibitor according to claim 2, wherein Ap is phenyl, tolyl or methoxyphenyl.

4. The inhibitor according to claim 1, in which A is:

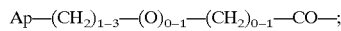

wherein Ap is an optionally substituted aryl group.

5. The inhibitor according to claim 4, wherein Ap is benzoyl, phenylacetyl, benzyloxycarbonyl, 3-phenylpropanoyl, 4-phenylbutanoyl, or 2-(benzyloxycarbamoyl)-3-(2-imidazolyl)-propanoyl.

6. The inhibitor according to claim 1, in which B is:

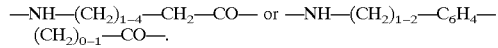

7. The inhibitor according to claim 6, wherein B is 6-imino-hexanoyl, 5-iminopentanoyl, 4-iminobutyryl or m-(iminomethyl)benzoyl.

8. The inhibitor according to claim 1, in which B' is:

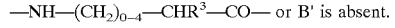

9. The inhibitor according to claim 1 wherein D is the residue of an amino acid selected from the group consisting of phosphoserine, aspartic acid, glutamic acid and γ-carboxyglutamic acid; or a salt thereof.

10. The inhibitor according to claim 1, wherein $Z^2$ is a direct bond, and at least one of B and B' contains a $CH_2$ group.

11. A composition containing an inhibitor according to claim 1, together with a pharmaceutically acceptable carrier.

12. A method of assaying protein:prenyl-transferase activity in a biological sample or any other prenyl-pyrophosphate consuming enzyme, comprising contacting said sample with a peptide analogue according to claim 1, and detecting the interaction of said peptide analogue with the enzyme under investigation.

13. A method of inhibiting PFT (protein farnesyl transferase), comprising contacting PFT with a compound according to claim 1 for a time and under conditions effective to inhibit PFT.

14. A method of inhibiting PFT, comprising administering a compound according to claim 1 to a mammal in need thereof for a time and under conditions effective to inhibit PFT.

15. A method of inhibiting PFT in a mammal that is afflicted with osteoporosis, atherosclerosis, restenosis, or cancer, comprising administering a compound according to claim 1 to said mammal for a time and under conditions effective to inhibit PFT.

16. A method of inhibiting PGGT-1, (protein geranylgeranyl transferase-1) comprising contacting PGGT-1 with a compound according to claim 1 for a time and under conditions effective to inhibit PGGT-1.

17. A method of inhibiting PGGT-1, comprising administering to a mammal in need thereof a compound according to claim 1 for a time and under conditions effective to inhibit PGGT-1.

18. A method of inhibiting PGGT-1 in a mammal that is afflicted with osteoporosis, atherosclerosis, restenosis, or cancer, comprising administering a compound according to claim 1 to said mammal for a time and under conditions effective to inhibit PGGT-1.

19. A method of inhibiting proliferation of tumor cells, comprising administering to a mammal in need thereof a compound according to claim 1 for a time and under conditions effective to inhibit protein farnesyl transferase.

20. A method of inhibiting proliferation of arterial smooth muscle cells, comprising administering to a mammal in need thereof a compound according to claim 1 for a time and under conditions effective to inhibit protein farnesyl transferase.

* * * * *